United States Patent [19]
Doherty et al.

[11] Patent Number: 5,745,051
[45] Date of Patent: *Apr. 28, 1998

[54] SURFACE MATERIAL AND CONDITION SENSING SYSTEM

[76] Inventors: John A. Doherty, 829 St. Andrews La., Louisville, Colo. 80027; Charles A. Kalbfleisch, 5 Deer Trail Rd., Boulder, Colo. 80302; Donald P. Keathley, 5 Oxford Dr., Middlefield, Conn. 06455; William J. Collins, 3053 S. Boston Ct., Denver, Colo. 80231

[*] Notice: The term of this patent shall not extend beyond the expiration date of Pat. No. 5,619,193.

[21] Appl. No.: 783,556

[22] Filed: Jan. 14, 1997

Related U.S. Application Data

[63] Continuation of Ser. No. 660,232, Jun. 7, 1996, Pat. No. 5,619,193.
[51] Int. Cl.$^6$ ............................................. G08G 1/09
[52] U.S. Cl. ........................ 340/905; 340/580; 340/581
[58] Field of Search ............................. 340/901, 905, 340/580–583, 436

[56] References Cited

U.S. PATENT DOCUMENTS

| | | | |
|---|---|---|---|
| 4,274,091 | 6/1981 | Decker | 340/905 |
| 4,492,952 | 1/1985 | Miller | 340/439 |
| 4,678,056 | 7/1987 | Kobari et al. | 180/247 |
| 5,416,475 | 5/1995 | Rendon | 340/905 |
| 5,416,476 | 5/1995 | Rendon | 340/905 |
| 5,447,272 | 9/1995 | Ask | 239/7 |
| 5,521,594 | 5/1996 | Fukushima | 340/905 |
| 5,619,193 | 4/1997 | Doherty et al. | 340/905 |

OTHER PUBLICATIONS

Data sheet D251, Aanderaa Instruments, Mar. 1995.
UCRL-MI-120916, Lawrence Livermore National laboratory, Jun. 7, 1995.

*Primary Examiner*—Jeffery Hofsass
*Assistant Examiner*—Daniel J. Wu
*Attorney, Agent, or Firm*—Holland & Hart LLP

[57] ABSTRACT

A system and apparatus for detecting and evaluating surface conditions on a road surface from a moving vehicle as disclosed. The system comprises a sensor means for detecting the presence of deposited material on a road surface, detecting means for determining one or more characteristics of the material such as its freezing temperature, process means for converting a detected signal and display means for displaying the condition of the road surface. A first embodiment of the invention includes a collection device for collecting a sample of the surface materials and one or more sensors to detect the freezing point of the material. A second embodiment includes a collection chamber which can be isolated and its contents frozen so that the freeze temperature may be obtained irrespective of knowing the composition of the material. A third embodiment of the present invention includes a remote sensing apparatus which utilizes electromagnetic radiation to sense actual surface material conditions, temperatures, and composition. This information is then processed through a computer in order to determine, preferably while the vehicle is in motion, those additional steps necessary to apply additional materials to the road surface in order to minimize hazardous driving conditions.

34 Claims, 9 Drawing Sheets

SURFACE MATERIAL AND CONDITION SENSING SYSTEM

CROSS REFERENCE TO RELATED APPLICATIONS

This application is a continuation of application Ser. No. 08/660,232 filed on Jun. 7, 1996, now U.S. Pat. No. 5,619,193, which is related to and claims the benefit of priority of U.S. Provisional Patent Application Nos: 60/00040, filed Jun. 8, 1995 and 60/004,941 filed Oct. 6, 1995.

BACKGROUND OF THE INVENTION

1. Field of the Invention

This invention generally relates to vehicle mounted sensor systems and more particularly to a system for determining characteristics of surface material related to adverse driving conditions from a vehicle.

2. Description of Related Art

A number of attempts have been made to sense the conditions of roadways, aircraft runways, and other surfaces for vehicular traffic, during changing adverse weather conditions For example, it is known to place conductivity, temperature and other sensors either in the road surface or adjacent the road to monitor the temperature of the road surface and/or monitor whether there is ice forming on the surface. This information is fed to the center for control and dispatch of trucks to apply salt or sand or other deicing mixtures. At airports these types of warning systems are used to inform maintenance crews that the runways need to be treated or alert the staff that deicing procedures need to be implemented. Some conventional systems have a supply of chemicals and pumps beside the roadway to automatically spray the road when triggered by a sensor.

There is also a need for such a warning system on road vehicles such as cars and trucks to detect pending adverse conditions. However, available mobile systems are limited to basic moisture detection and temperature monitoring systems. Some examples of such systems are disclosed in U.S. Pat. Nos. 4,492,952 and 4,678,056. One particular system, disclosed in U.S. Pat. No. 5,416,476, employs an infrared sensor which is mounted on the exterior of the vehicle and sends a signal to a microprocessor which then can display the temperature of the road surface. These systems are simplistic and do not tell the operator the critical information needed under all conditions, such as, at what temperature will the particular material actually on the road surface freeze? Therefore there is a need for a material sensing apparatus and system for determining when an actual liquid on a road surface will freeze and alerting the operator to such situations before they actually occur so that the operator can adjust driving techniques accordingly.

There is also a need for a mobile mounted sensing apparatus and system for use by road crews to evaluate existing material on a road surface in order to determine the amount of additional material to be applied to the surface in order to reduce the hazardous driving conditions.

SUMMARY OF THE INVENTION

The system in accordance with the present invention addresses the above described needs. It is thus an object of the present invention to provide a unique multipurpose system which includes a multipurpose sensor mounting platform accommodating a variety of sensors that enables the temporary use of materials such as rainwater and road conditioning materials actually encountered on a road surface to determine the condition of the road surface. It is another object of the invention to provide a system for detecting the actual materials on a roadway. It is another object of the invention to provide a system for determining a characteristic such as friction coefficients or the actual freezing temperature of a material on a road surface regardless of the makeup of the material. It is a still further object of the present invention to provide a reliable display of information to the vehicle operator of actual and pending conditions of the road surface. It is a still further object of the invention to provide an apparatus for sensing actual road conditions that can function automatically or manually.

It is a still further object of the present invention to provide a system for remote sensing and evaluation of material present on a roadway surface which includes a means for extracting sufficient information to determine the characteristics of the composition of the surface material and utilizing user input information to calculate the amount of additional material to be applied to the road surface to minimize the development of adverse conditions.

One embodiment of the apparatus for sensing surface material condition in accordance with the present invention comprises a collection means for receiving material discharged, for example, from a vehicle wheel in contact with a roadway surface, at least one sensing means coupled to the collection means for detecting a characteristic of the received material such as friction coefficients, temperature, conductivity, and chemical concentrations and producing a corresponding signal, processing means for converting the corresponding signal, and display means connected to the processing means for providing an indication of surface conditions based on the material characteristics.

The collection means may include a conventional mud flap located immediately behind a vehicle wheel so that a portion of any surface material that is picked up by the vehicle wheel and thrown against the flap may be collected. An alternative collection means is a scoop located in proximity of the wheel or adjacent the road surface to collect deposited surface material.

Another embodiment of the invention does not require a collection means, but instead, remotely senses directly the surface material characteristics such as temperature, conductivity, friction coefficients or chemical concentrations. This embodiment utilizes a sensor located on the undercarriage of the vehicle at a preferably fixed distance from the road surface which senses the surface temperature and at least one other unique surface material characteristic so that the specific material or materials can be identified, the composition determined, and freezing temperatures determined.

Another embodiment of the apparatus has a sensor mud flap which includes a channel leading into a detection chamber where liquid runoff from the wheel flap is periodically collected and then frozen. The freeze point is sensed along with the temperature of the collected material. This information is displayed to the operator of the vehicle. Once the freeze point is determined, the frozen material is thawed and discharged from the chamber so that a new sample may be collected and analyzed.

Another embodiment of the invention includes an endless belt of liquid absorbing material mounted to the flap. The endless belt collects and absorbs liquid collected by the flap, transports it to a collector which extracts the liquid from the belt and directs it to the sensor means which also can be a detection chamber where the chamber contents is frozen in order to sense the freeze point.

The sensing means may be a single sensor or a combination of several sensors to detect particular parameters of interest. The road conditions are primarily affected by changes in temperature and material concentrations. Therefore the sensing means may include resistance temperature detectors, thermocouple, infrared temperature sensors, conductivity detectors, close proximity electromagnetic radiation (EMR) transmitters and detectors or transceivers, friction measurement devices, and other material analysis systems such as a spectrographic analysis system such as a mass spectrometer. In the latter case, the mass spectrometer or other material analysis device would preferably be mounted inside the vehicle, with a sample conveying means such as a belt or pump line directing the sample from the flap or other collection platform such as a scoop, etc. into the analysis device, e.g., the vaporizing chamber for the spectrometer. Alternatively, an ultra wide band doppler radar or any other suitable electromagnetic radiation (EMR) emission and detection technique may be used to remotely ascertain chemical and physical characteristics of the material on the roadway surface. As used in this specification, the term "electromagnetic radiation" means a series of waves that are propagated by simultaneous periodic variations of electric and magnetic field intensity and that include radio waves, infrared, visible light, ultraviolet, X rays, and gamma rays.

The processing means may include a microprocessor for converting sensed signals to display signals, store potential material data, determining material identity and pertinent material characteristics, and includes power and signal transmission means.

The display means may be a panel with indicators of the freeze point, the ambient temperature, and connections to more detailed signal analysis equipment such as chart recorders, tape recording devices, or other processing equipment. The display means may also include alarms and inputs to automatic functions such as activating anti-lock brake systems, or transfers from two wheel to all-wheel drive systems, or activating chemical spreader control functions, etc.

These and other objects, features, and advantages of the system and apparatus of the present invention will become more apparent from a reading of the following detailed description when taken in conjunction with the accompanying drawing figures.

DETAILED DESCRIPTION OF THE INVENTION

First Embodiment

Figure 1:
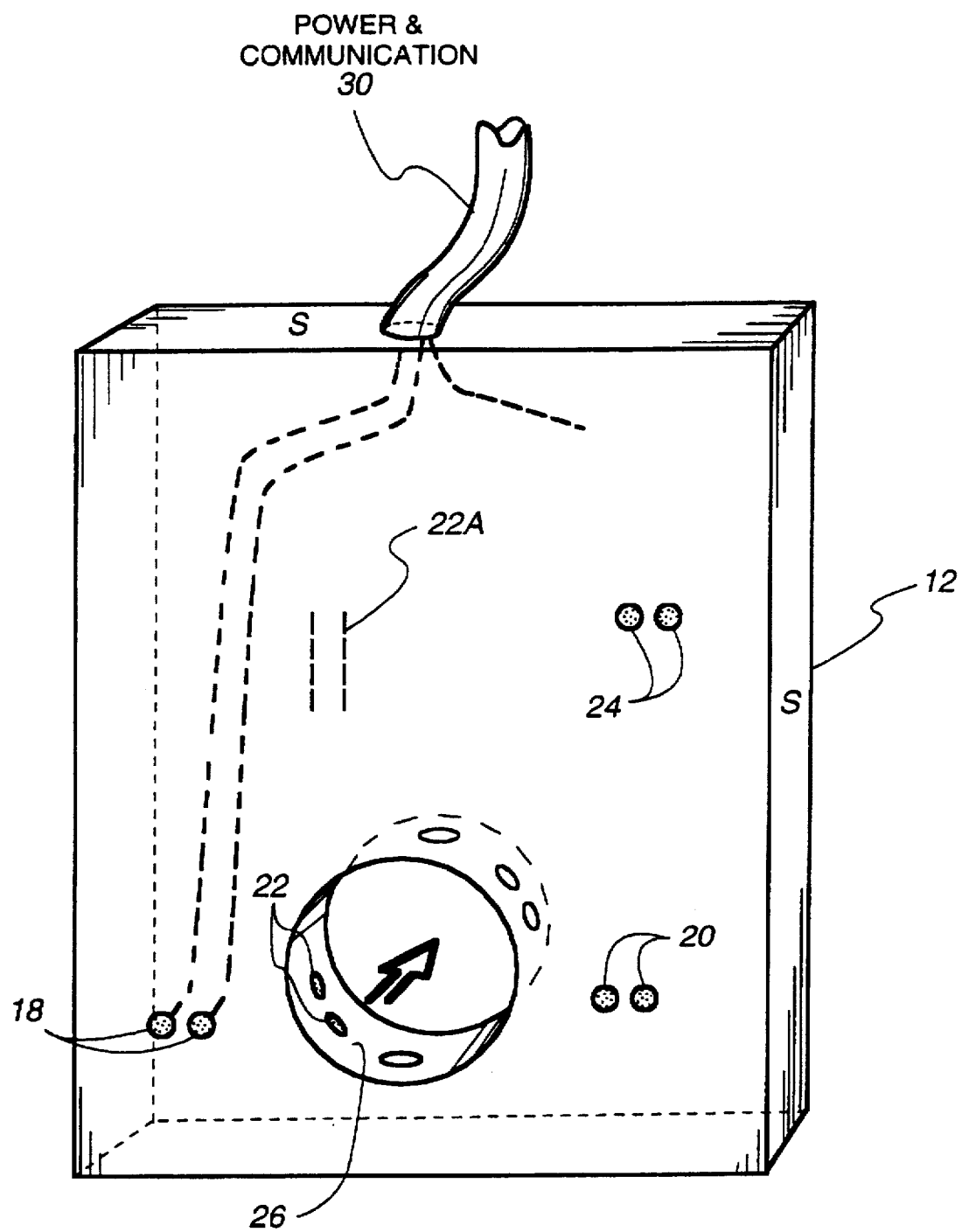
FIG. 1 is a perspective schematic view of a sensor platform in accordance with a first embodiment of the invention.
Figure 2:
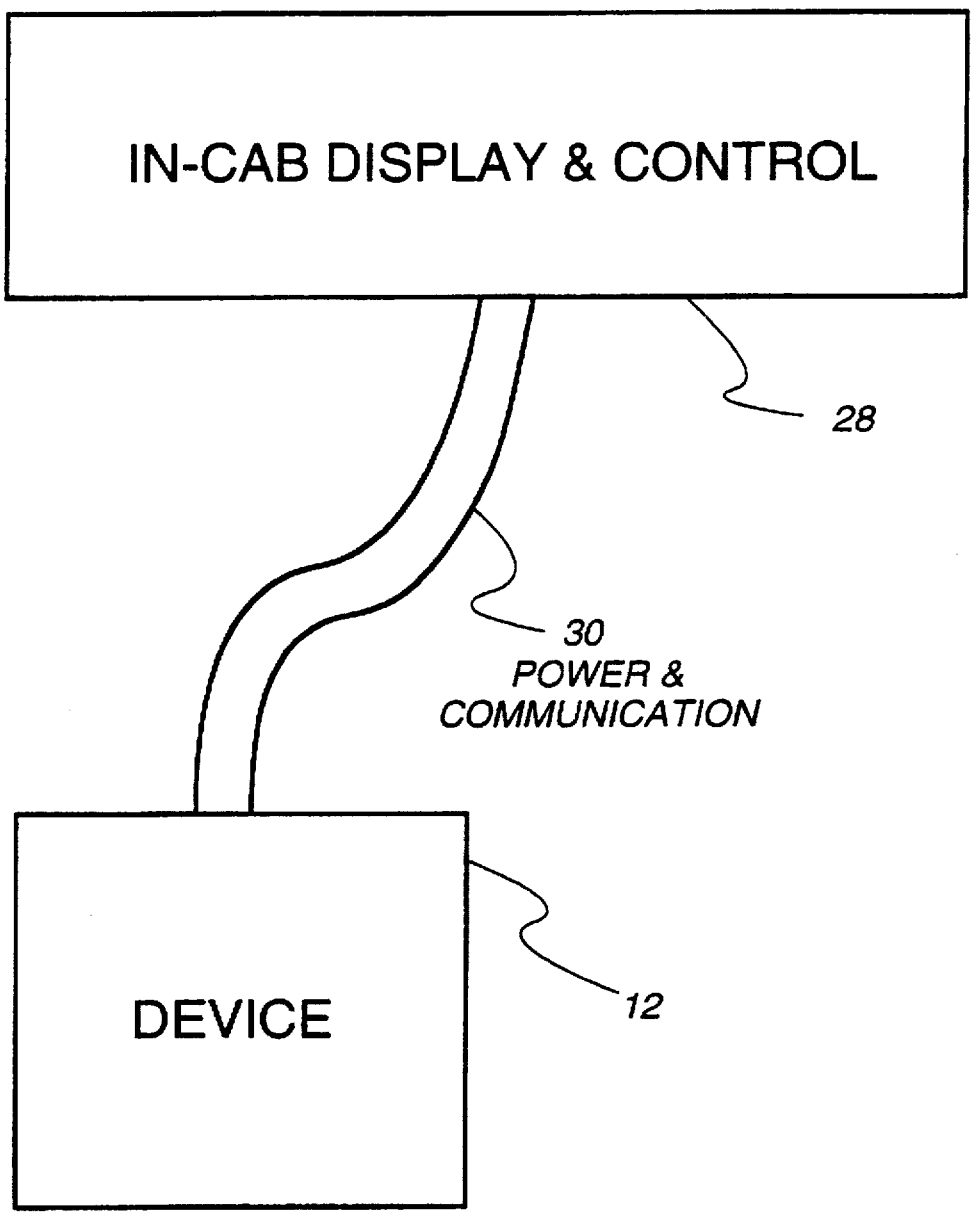
FIG. 2 is a block diagram of the first embodiment of the system in accordance with the invention.
Figure 3:
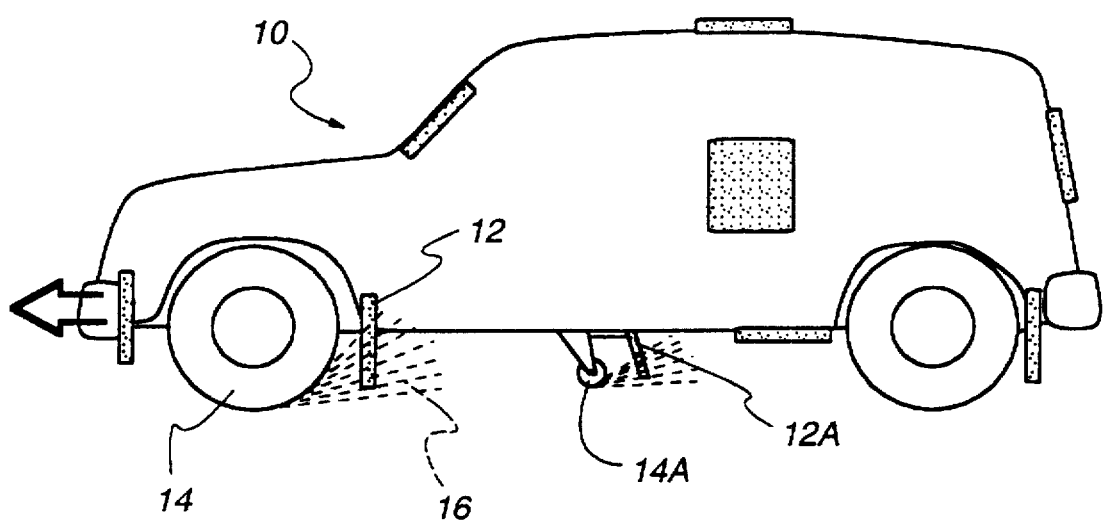
FIG. 3 is a schematic side view of a vehicle showing potential locations for the sensor platform in accordance with the present invention.

Referring now to FIGS. 1 through 3, a first embodiment of the apparatus of the invention includes a platform 12 which is typically vertically mounted behind a vehicle wheel 14. This platform 12 replaces and also operates as a conventional mud flap on the vehicle 10.

As stated above, one of the objects of this invention is to provide a unique multi-purpose mounting platform 12, such as is shown in FIG. 1, that enables the temporary use of materials 16 which are typically discharged from a vehicle wheel/road surface interface to measure certain characteristics of the materials that have left a roadway surface (surface materials), and to also determine certain characteristics of the surface itself. The surface is most commonly a road or aircraft runway surface. Throughout this specification, use of the terms surface, road, roadway, or runway are interchangeable and are used to generally mean any surface upon which a vehicle is operated or is operable.

The manipulation of the characteristics of surface materials, for instance freezing the surface material, is one efficient and accurate way to obtain information on the surface conditions as well as determine the conditions of loose surface material.

The characteristics to be measured may include but are not limited to:

1. Material volumetric buildup, such as snow, ice, liquid solution, i.e., depth of material on the surface.

2. Determination of the constituents of the chemical solutions and mixtures present, and characteristics of the solutions and mixtures, such as percent of a particular chemical in solution, the freezing point (temperature) of the solution, and the amount or percentage of a component in the solution and/or mixture.

3. Temperatures, both ambient and of the material solution or mixture sensed.

The methodology of determining the characteristics described above varies with the characteristic being tested. For example, the general type of material buildup may be measured via resistivity and/or conductivity in conjunction with temperature. The chemical composition of the material on the road surface may be determined by spectrographic techniques, or by evaluation of EMR reflections. The percent of chemical(s) in a solution that has built up on a road surface may be determined by measuring the resistivity and/or conductivity of the collected material covering the sensor or by evaluation of EMR reflections. The freeze point of the solution may be determined by a software comparison, such as a table look-up, when the material components are known. The ambient temperature is measured via a thermometer or thermocouple which could be remote from the platform. The temperature of the solution/material buildup is measured by any known appropriate sensor means such as a thermometer, thermocouple or infrared sensor preferably mounted on the platform 12.

Alternatively, the freeze point of a solution can actually be determined by actually freezing the collected solution. The freeze point is determined by monitoring a property of the solution that indicates that the freezing temperature is reached, such as changes in electrical conductivity. This could eliminate the need for a look-up table.

The sensor platform 12 can be made of a thermoplastic material, or sensor flap material such as urethanes or teflon, and which preferably has the following characteristics:

impact/abrasion resistant;

low surface friction to maintain slipperiness to sheet the discharged material off of flap and sensor surface(s);

pliable and flexible temperature range of plus 150–minus 40 F. degrees without melting or becoming brittle. Operating temperature of eighty degrees fahrenheit (80° F.) to minus forty degrees fahrenheit (−40° F.); and capable of using all sides for mounting of sensors and to be formed in such a way as to make sure that sensed material will be directed to the various surfaces as needed.

The sensor platform or flap 12, shown in FIG. 1, illustrates a variety of sensors mounted on or within it to illustrate the various mounting configurations for the purpose of making measurements or sensing certain characteristics of the material that has left the road surface as a result of turbulence or surface discharge behind the vehicle wheel.

The platform 12 is constructed to carry or have imbedded therein various sensors 18, 20, 22, and/or 24. These sensors, depending on their function, may protrude outside of or be recessed within the finished flap 12 so that they will be exposed to, or not exposed to, the material to be sensed, or will have access to the material to be sensed. As an alternative, the various sensors could be mounted with appropriate hardware onto an existing piece of flap material to achieve the same effect.

For example, sensors 18 and 20 may be a conductivity detector and/ or a resistance temperature detector (RTD) or a thermocouple (TC) which senses the temperature of the material on the surface of the flap 12 and the presence of conductive solutions in the material such as NaCl or KCl or MgCl$_2$ in order to determine the type of material buildup. The lead wires from the conductivity cell and/or the RTD or TC are either embedded in or mounted behind the flap 12 for protection from abrasion and moisture.

Sensor 22 may be a sensor such as an RTD or TC mounted within an aperture 26 in the flap 12. The aperture 26 permits the passing air flow behind the wheel 14 to blow clear and thus ensure that new material continuously passes the sensor location. Other sensor locations in the aperture 26 are shown in dashed lines. The aperture 26 may also be used to direct flow of material past a sensor such as an EMR device.

The sensor 22A may alternatively be embedded in the flap 12 with the tip projecting to the front surface of the flap 12 to accurately measure the captured material temperature.

Sensor 24 may be a RTD or TC mounted either behind the flap 12 or embedded within it so as to be representative of the ambient temperature of the flap 12. Alternative sensor locations may be incorporated into the sides or top of the flap 12 as indicated by the "S" thereon.

The flap 12 is preferably mechanically attached to the vehicle 10. The sensor flap 12 is designed to temporarily "catch" the discharge material from the vehicle's wheel 14. Alternatively, a separate sensor wheel 14A may be provided as shown in FIG. 3, for producing material discharge to be collected by a flap 12A which carries the sensors for making the measurements concerning the surface that the vehicle is riding over as well as detecting any buildup that might be on the surface—even after the buildup has left the surface.

The incident spray material must not cling to the flap or plug any pass-through holes as new samples must periodically be measured/sensed. Therefore, proper material selection is an important consideration in this first embodiment.

The sensors are connected to an in-cab display and control panel 28 via a cable 30 as shown in FIG. 2. The control panel 28 is capable of controlling, communicating with, and powering the sensors as well as interpreting sensor data and preferably includes display/input devices which can display information, accept outside input, store commands, and retrieve data. Alarm and control functions are also displayed on this panel. For example, interpreted data could include a freeze point prediction or alert notice for the measured solution and/or material.

Second Embodiment

A second embodiment of the surface condition sensing system in accordance with the invention is shown in FIGS. 4–7. The system in accordance with the second embodiment is specifically directed to determining the freezing temperature of a surface material. It includes an apparatus 38 that collects material from the road surface into a chamber, freezes it, determines the freezing temperature, communicates the data appropriately to a display/control console, and then thaws the material, empties the chamber, and prepares for the next measurement cycle. The apparatus 38 is mounted in a location on the platform 12 as disclosed above.

Figure 4:
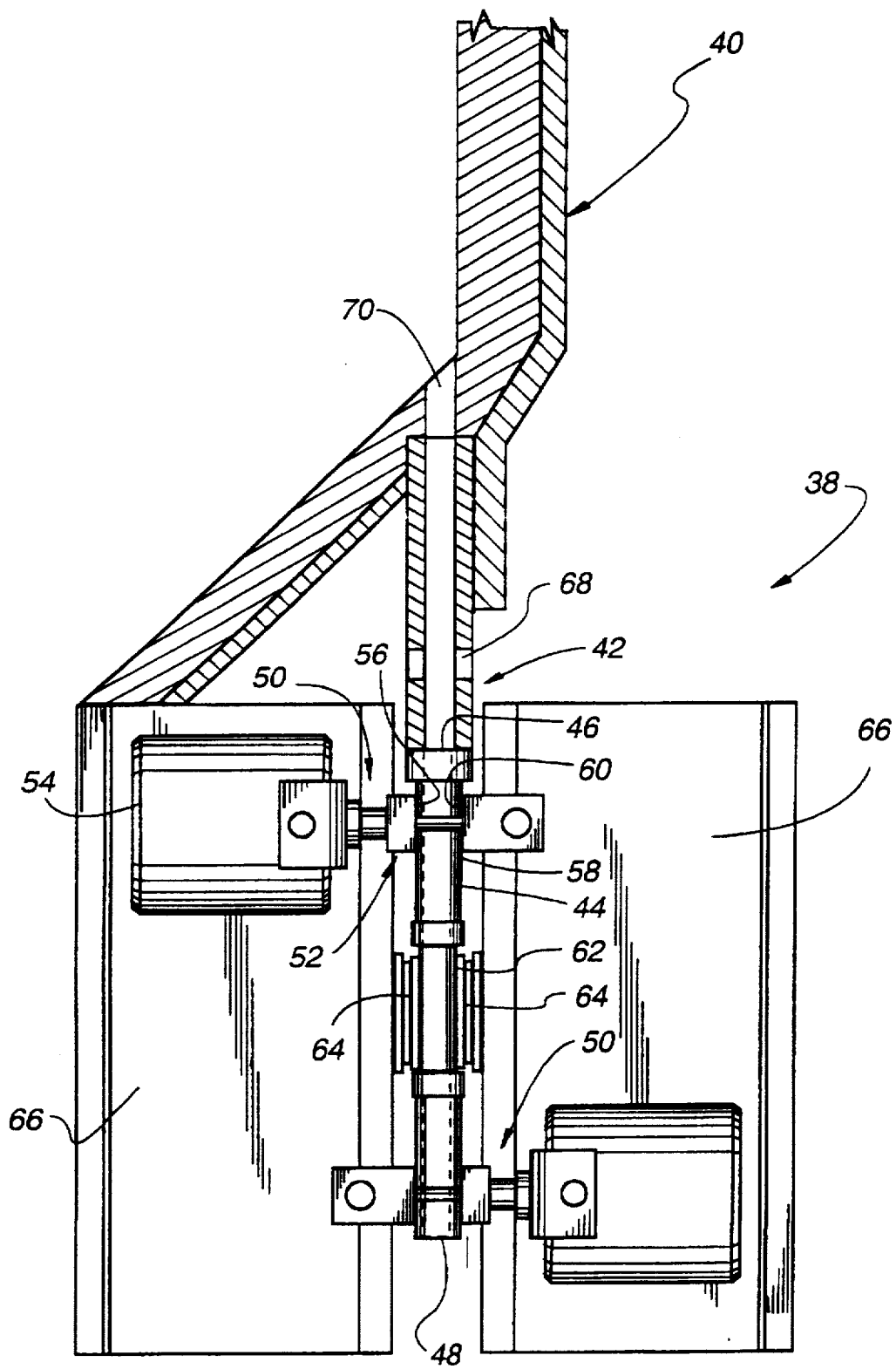
FIG. 4 is a partial side view of a second embodiment of a sensor platform of the present invention.

The apparatus 38 associated with this system is seen in a side view in FIG. 4. The apparatus 38 comprises a support structure 40 made of any suitable material, for instance a laminate of a thermoplastic material and aluminum, and a capture and measurement portion 42 supported below and from the support structure 40. The capture portion 42 comprises an elongated chamber 44 having an open top end 46 and an open bottom end 48 generally having an elongated oval cross section. The open top end 46 is for receiving any surface material that collects above the top end 46 on the support structure 40.

The top end 46 and bottom end 48 of the chamber 44 are preferably made of a flexible material, such as plastic or rubber, which is preferably able to be selectively opened and pinched closed to allow material to flow in and out as desired. Selective opening and closing valve mechanisms 50 are mounted to the apparatus at the appropriate positions adjacent the upper and lower ends 46 and 48. When the bottom end 48 is closed and the top end 46 is open, collected material builds up in the chamber 44. When both ends are closed, the collected material is isolated. When both ends are open, the collected material is discharged from the lower end 48.

Each of the opening and closing mechanisms 50 includes a pinch valve 52 and a solenoid 54. The top and bottom ends 46, 48 of the chamber 44 are selectively opened and closed by pinch-valves 52. When the upper solenoid 54 is energized, it extends a shaft 55 outward and pushes a first surface 56, engaging a flexible portion 58 of the chamber 44 adjacent the upper open end 46, from one side and drives the flexible portion 58 towards the other side, which is in contact with a stationary second surface 60. The open top end 46 of the chamber is thus pinched closed between the first and second surfaces 56 and 60, causing a preferably impermeable seal to be formed at the top end of the chamber. The bottom end 48 of the chamber 44 is closed in a similar manner using a second solenoid operated pinch valve 52.

The chamber 44 has a central portion 62 of a predetermined length and width between the selective opening and closing mechanisms 50. This portion 62 preferably has an elongated oval cross section and is made of a conductive material, such as copper. The central portion 62 of the chamber 44 comprising a conductive material is thermally coupled to opposing plates of a thermo-electric heater/cooler 64 which controls the temperature of the central conductive chamber 44 using, for example, the well known Peltier effect.

A heat sink 66 surrounds the chamber 44, preferably on all sides, along the length of the chamber 44 to facilitate the heating and cooling process as a result of the operation of the thermo-electric heater/cooler 64.

A liquid exiting aperture 68 is formed in the chamber 44 above the first surface 56 to allow any surface material draining into the liquid capture gap 70 to exit the chamber 44 when the flexible portion 58 of the chamber 44 is closed during operation of the thermo-electric heater/cooler 64. The draining liquid flows down over the heat sinks 66, preferably thereby beneficially affecting the heat transfer capabilities of the heat sinks 66.

Operation

The operation of this second apparatus may be either automatic or manual. In automatic operation, the apparatus operates continuously or at a predetermined cycle frequency as determined by the user. In manual mode, the user actuates the apparatus each time road surface condition information is desired. This second embodiment of the road surface sensing system is used to collect surface material and accurately determine the freezing point of such material regardless of material composition.

The apparatus is positioned on the vehicle such that it is exposed to the spray of the surface material caused by the motion of the vehicle, as is schematically shown in FIG. 3. The apparatus may be positioned behind front or rear wheels, or may optionally include a separate wheel or scoop device to pick up material from the road surface.

Figure 5:
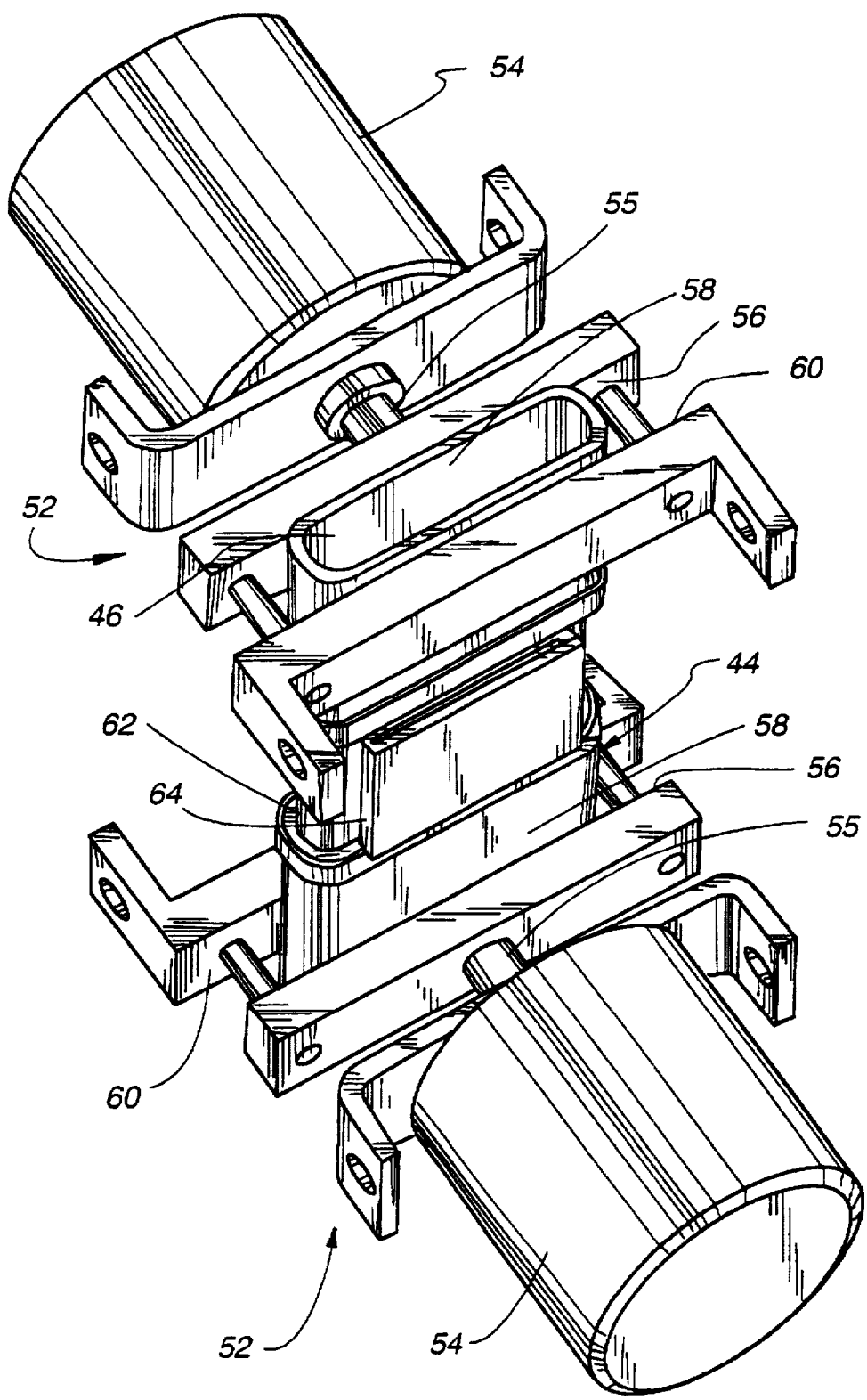
FIG. 5 is a perspective view of the second embodiment of the present invention.

Referring now to the perspective view of the apparatus 42 in FIG. 5, when a measurement is to be taken, the bottom end 48 of the chamber 44 is closed. The surface material spray contacts the support structure 40, runs down the support structure 40 under the influence of gravity into the liquid capture gap 70. The surface material collects in the chamber 44 either for a programmable predetermined period of time, preferably about 5 to 10 seconds, or until the appropriate liquid level is obtained, at which time the top end 46 is closed by closure of the upper pinch valve 52 to preclude entry of material that could contaminate the sample during measurement.

When a sufficient amount of surface material is collected in the chamber 44 and the upper pinch valve 52 is closed and the thermo-electric cooler 64 is activated to freeze the collected surface material. The electrical conductivity of the collected surface material is monitored in the chamber 44 during the cooling process to establish the freezing point of the surface material. This freezing point is communicated appropriately to the processor and display console 72, shown in FIG. 7.

After the freezing point is determined, the thermo-electric cooler 64 is activated to heat the conductive chamber portion 62 to melt the surface material. The bottom end 48 is then opened by de-energizing the lower pinch valve 52 to allow the surface material to exit the chamber 44. The process can then be repeated to obtain a new reading.

Figure 6:
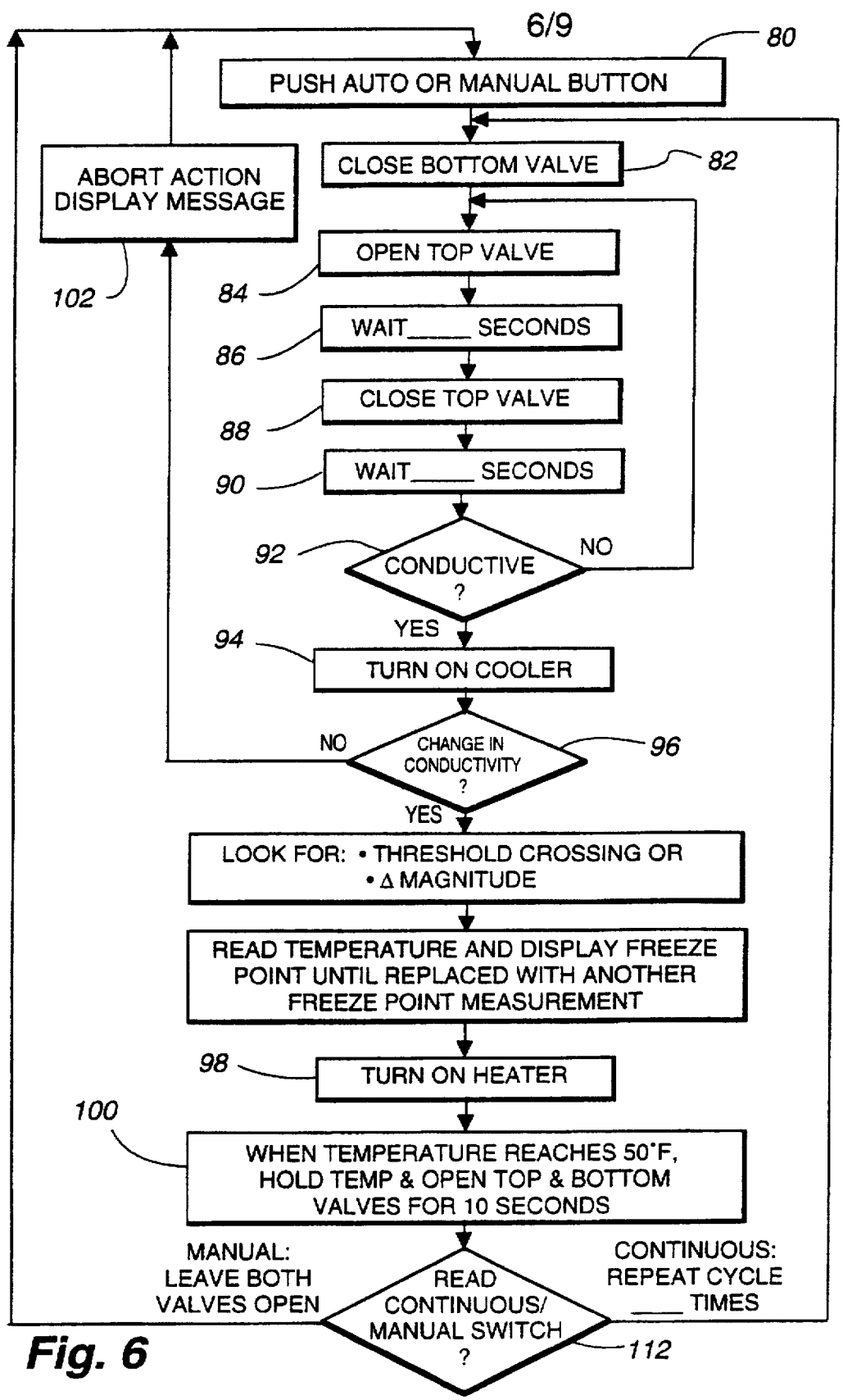
FIG. 6 is a control block diagram of the second embodiment of the present invention.

More particularly, referring to FIG. 6, and to FIG. 7, automatic operation of the apparatus in accordance with this embodiment of the invention proceeds as follows. The user places the automatic/manual selector switch 80 in the automatic position. When the switch 80 is placed in the automatic position, a signal 82 is sent to close the bottom valve and a signal 84 is provided to de-energize the upper solenoid valve 52 so that collected material may flow into the chamber 44. The control system then pauses for a predetermined amount of time, such as ten seconds, in block 86.

At the expiration of this wait period, a signal 88 is sent to close the upper valve 52 in order to isolate the sensing portion 62 of the chamber 44. Preferably, another programmable wait period 90 of a predetermined length of time is conducted after which the processor tests whether the contents of the central portion 62 of the chamber 44 is conductive. This test of conductivity 92 is necessary in order to sense whether there is any material collected in the chamber. If the material collected in the chamber is conductive, a signal 94 is sent to turn on the thermo-electric heater/cooler 64 in the cooling mode. Conductivity is continually monitored in block 96 to determine a significant change in conductivity, as the material in the central portion 62 of the chamber 44 is cooled, which indicates that the threshold to freezing has been reached. This threshold is normally indicated by a substantial change in magnitude of the conductivity signal. If the threshold of freezing is detected in block 96, the processor then sends a signal 98 to turn on the heater until it reaches a temperature substantially greater than the threshold, for example, about 50° Fahrenheit. When this temperature is reached, a control signal 100 is sent to de-energize both upper and lower solenoid valves 52 for a programmable period of time sufficient to permit the collected material to drain from the chamber 44, for example, ten seconds.

On the other hand, if, in block 96, no threshold crossing was sensed, an abort action display message signal 102 is displayed and the automatic process steps 80 through 96 are repeated.

Figure 7:
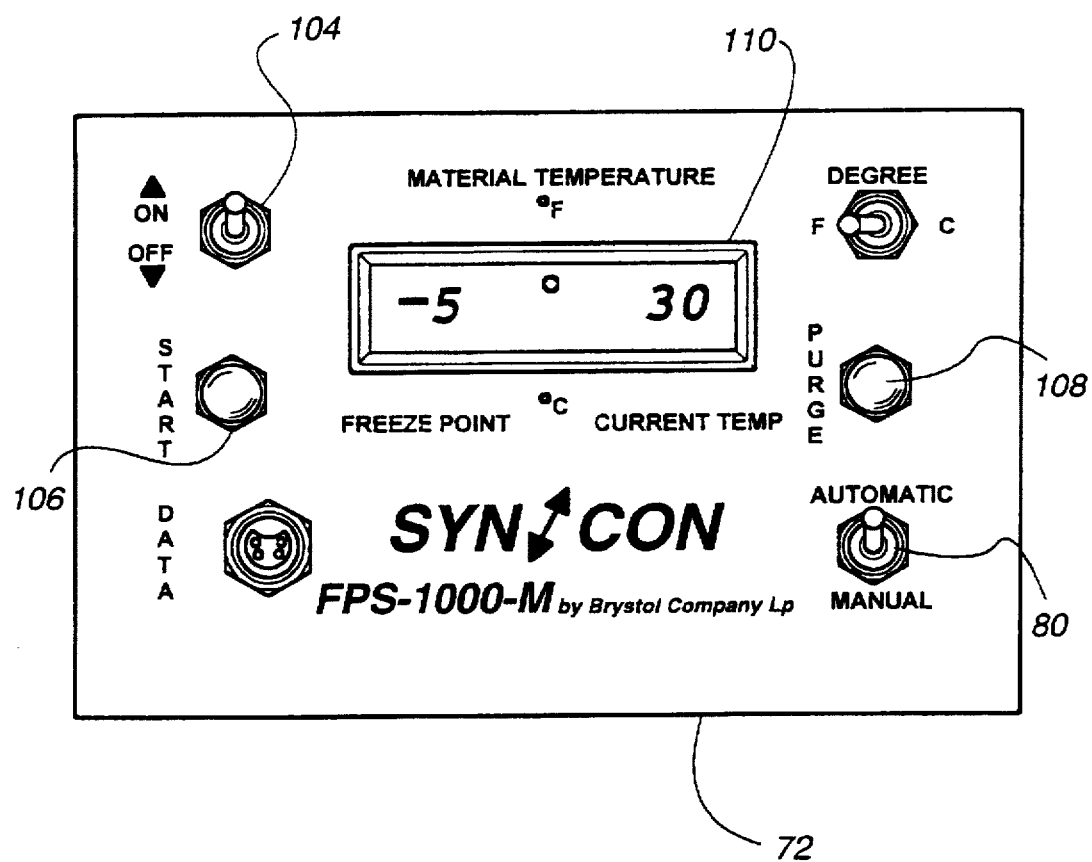
FIG. 7 is front view of the display panel in the second embodiment of the present invention.

Referring now to FIG. 7, the display console includes an on/off switch 104, a start switch 106, a purge switch 108, and a display 110. Manual operation or automatic operation is selected by switch 80. When the manual operation is selected, the purge switch 108 may be pressed by the operator. This de-energizes both inlet and outlet valves 52, allowing any materials contained in the chamber 44 to be discharged. The start switch 106 is pressed and the automatic or manual control process shown in the flow chart in FIG. 6 is performed from block 82 through block 100. After the chamber temperature has reached 50° in block 100, the processor determines in block 112 whether switch 80 is in the automatic or manual position. If in the manual position, a signal is sent to leave both valves 52 open and await further manual instructions. If switch 80 is in the automatic position, however, the process is automatically directed to block 82 in which the bottom valve 52 is closed and the sample collection and evaluation process is repeated a programmable number of times.

Figure 8:
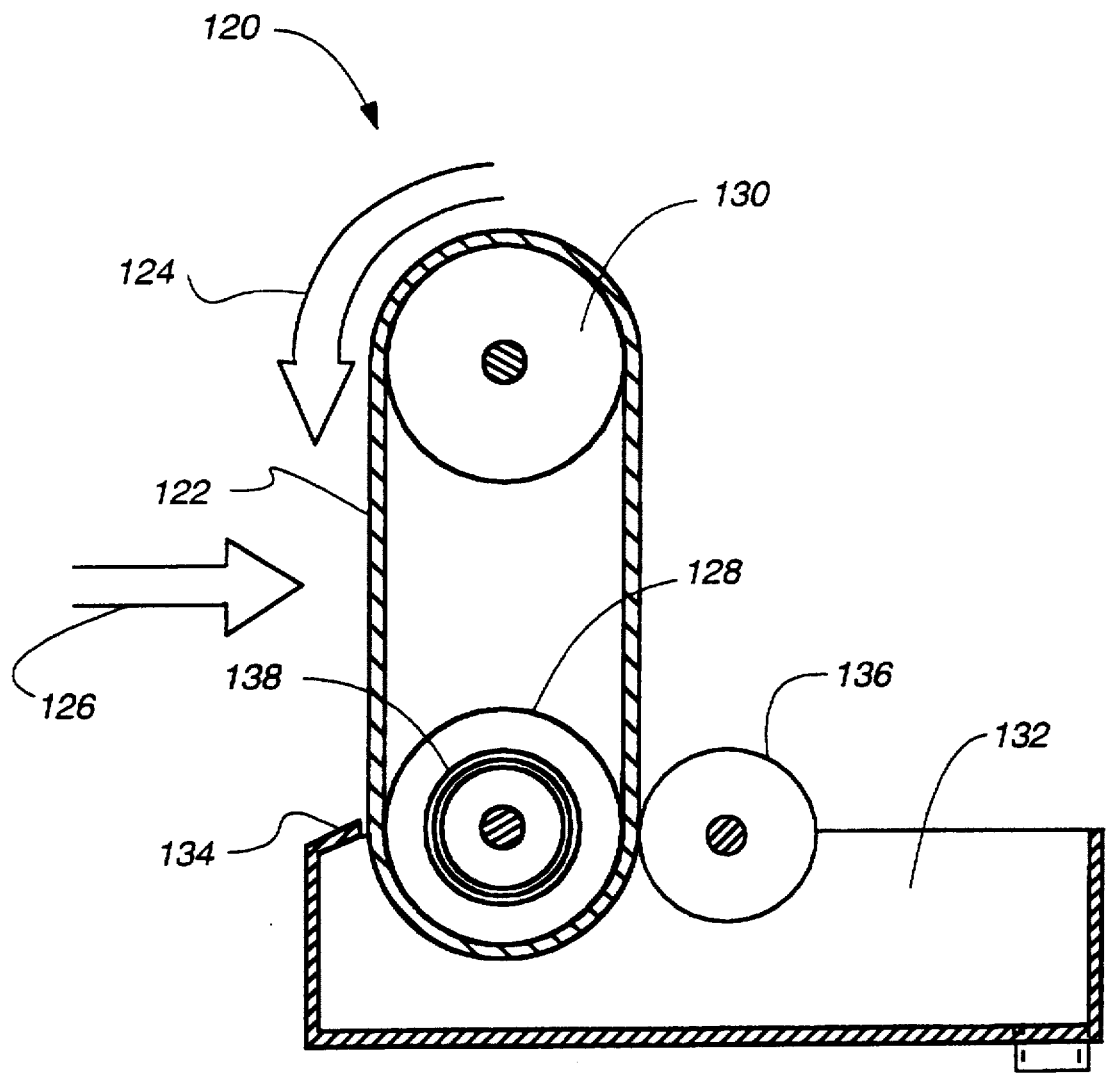
FIG. 8 is a schematic side view of an alternative collection apparatus of a system in accordance with the present invention.

Referring now to FIG. 8, the apparatus in accordance with the second embodiment may be modified to include a collection apparatus 120 that incorporates an endless belt 122. In operation, the endless belt 122 moves in the direction of the arrow 124. Road debris thrown up by the vehicle moves and impinges on belt 122 in the direction shown by arrow 126. The lower pulley 128 is preferably either hydraulic motor driven or electrically driven. The upper pulley 130 is preferably spring biased away from the motor driven pulley 128 to maintain tension on the belt 122. A collection hopper 132 is positioned below the motor driven pulley 128 and discharges into the open upper end 46 of the collection chamber 44 above described. A scraper 134 is positioned adjacent the front facing portion of the belt 122 before the belt 122 enters the hopper 132 so that as it enters the hopper 132, leaves and other solid debris may be scraped from the belt 122.

A pinch idler pulley 136 is mounted adjacent the motor driven pulley 128. As the belt moves around the pulleys counterclockwise as shown in FIG. 8, liquid picked up from the road is "squeegeed" into the hopper 132 as the belt 122 passes between idler pulley 136 and driven pulley 128. A spring-loaded clutch 138 may also be provided on the motor driven pulley so that the collection apparatus 120 does not operate while the central portion 62 of the collection chamber 44 is isolated.

Third Embodiment

Figure 9:
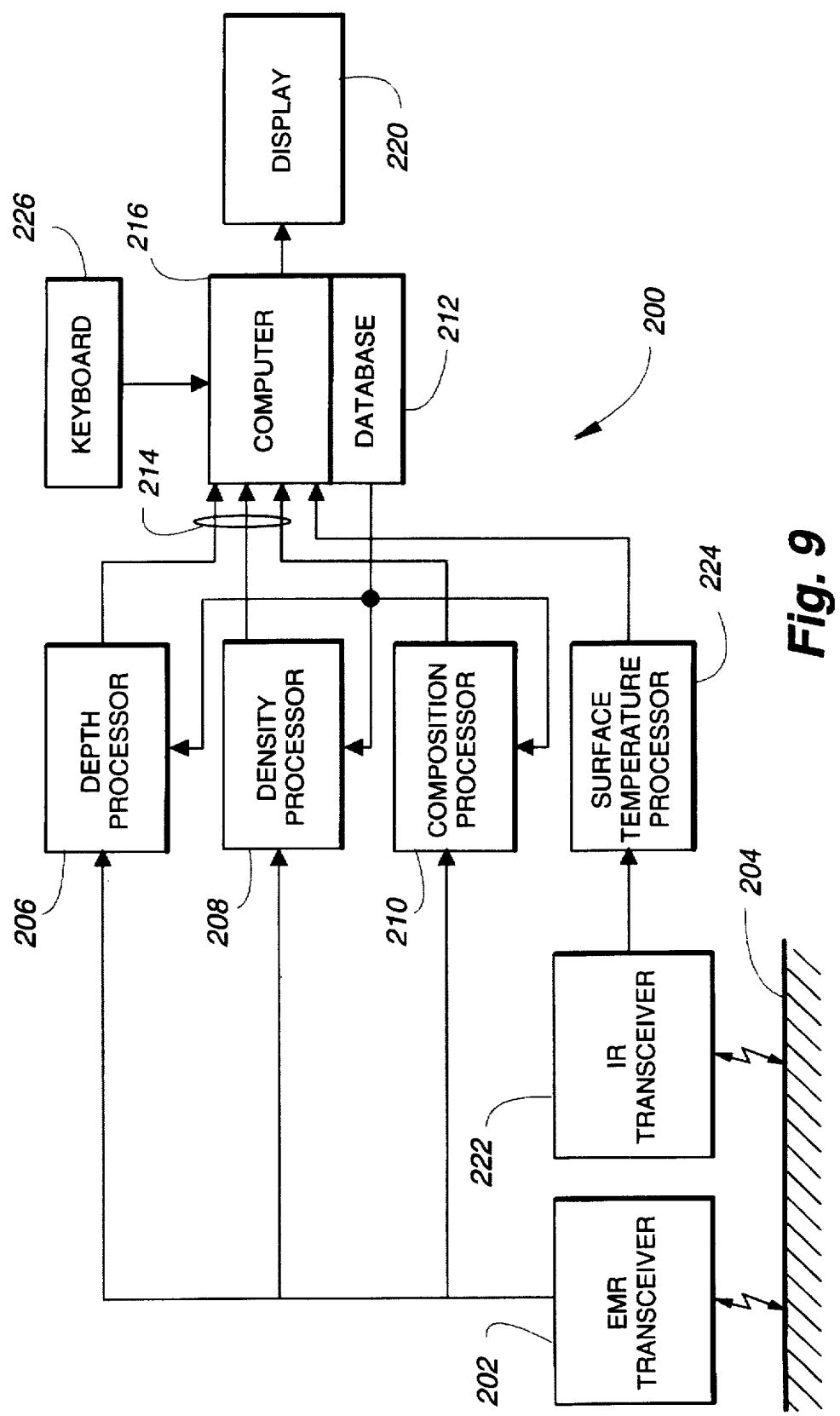
FIG. 9 is a block diagram of a remote sensing embodiment of the system in accordance with the present invention.

A block diagram of a third embodiment of the sensing system in accordance with the present invention is illustrated in FIG. 9. This third embodiment is a completely remote sensing apparatus which is mounted on the vehicle. This system 200 includes at least one electromagnetic radiation transceiver 202 which emits a ultra-wide band (UWB) impulse radar. A very short electromagnetic impulse is propagated from transceiver 202 and echoes that reflect from the road surface 204 are evaluated. These reflected signals are set to a depth processor 206, a density processor 208, and at least a chemical composition processor 210. The EMR reflected pulse may be utilized directly by the depth processor 206 to determine the depth of any surface layer of material on the roadway. However, the density processor, and composition processors 208 and 210 rely also on input from a database 212 to determine, by comparison to peak height or phase shift of the reflected signal versus the incident signal, an output which is unique to a particular chemical composition and density. Comparing these outputs to the database content produces or can result in quantitative density and composition information 214 which is, in turn, fed to computer 216 along with depth information 218.

The depth 218 is processed in the computer 216 to provide a display 220 with information necessary to determine what additional chemicals need to be deposited on the road surface in order to minimize the hazardous conditions. In addition, the computer 216 may provide a direct output to a control device for automatically dispensing the appropriate amounts of chemicals to the road surface as the vehicle drives by.

An infrared transceiver 222 is also mounted on the vehicle and is directed toward the road surface. The transceiver 222 provides an output to a road temperature processor 224 which in turn also feeds an output to the computer 216 indicative of the actual road surface temperature.

The apparatus 200, in accordance with the third embodiment of the present invention, may be compactly designed for unitary installation in the cab of a road maintenance vehicle, such as a salt truck, with the display 220 and a keyboard input device 226 integrated into the dashboard of the vehicle. The driver can then input to the computer 216 desired deicing concentrations or other desired input information. The computer 216 then can compare the actual composition and status of the material actually on the road and either display or automatically control the dispensing of additional chemicals to the road surface.

The apparatus and system in accordance with the present invention has been described with reference to particular embodiments thereof. Therefore, the above description is by way of illustration and not by way of limitation. Accordingly, it is intended that all such alterations and variations and modifications to the embodiments are within the scope of the present invention as defined by the appended claims.

What is claimed is:

1. A system carried by a vehicle for remotely sensing and displaying at least one characteristic of a material deposited on a vehicle travel surface, said apparatus comprising:

an electromagnetic radiation transmitter mounted on said vehicle for transmitting a signal toward said material on said vehicle travel surface;

an electromagnetic radiation receiver mounted on said vehicle for receiving a first reflected signal from said vehicle travel surface and a second reflected signal from said deposited material on said vehicle travel surface;

at least one signal processor connected to said receiver for processing said first and second reflected signals and producing an output signal corresponding to at least one characteristic of said deposited material; and a computer connected to said processor generating a corresponding display signal.

2. The system according to claim 1 further comprising a second signal processor connected to said receiver and to said computer for processing at least one of said reflected signals and comparing the reflected signal to said transmitted signal to identify the composition of said deposited material and generate a composition output signal.

3. The system according to claim 2 further comprising a third processor connected to said receiver for comparing said reflected and transmitted signals to determine the density of said deposited material and generating a density output signal.

4. The system according to claim 3 wherein said computer receives said density output signal, said composition output signal, and calculates the amount of a user inputted composition needed to be applied to said vehicle travel surface to produce a desired composition on said surface.

5. The system according to claim 3 further comprising a temperature sensor mounted on said vehicle connected to a temperature processor for generating an output signal to said computer corresponding to the temperature of said vehicle travel surface.

6. A system carried by a vehicle for remotely sensing and displaying at least one characteristic of a material deposited on a vehicle travel surface, said apparatus comprising:

an electromagnetic radiation transmitter mounted on said vehicle for transmitting a signal toward said material on said vehicle travel surface;

an electromagnetic radiation receiver mounted on said vehicle for receiving a first reflected signal from said deposited material on said vehicle travel surface;

at least one signal processor connected to said receiver for processing said first reflected signal and producing an output signal corresponding to at least one characteristic of said deposited material; and a second signal processor connected to said receiver for processing said first reflected signal and comparing the reflected signal to said transmitted signal to determine another characteristic of said deposited material.

7. The system according to claim 6 further comprising a temperature sensor mounted on said vehicle connected to a temperature processor for generating an output signal corresponding to the temperature of said vehicle road surface.

8. The system according to claim 6 wherein one of said processors generates an output signal corresponding to the density of said deposited material.

9. The system according to claim 8 wherein said receiver receives a second reflected signal from said vehicle travel surface in order to generate an output corresponding to the depth of said deposited material on said vehicle travel surface.

10. A system carried by a vehicle for remotely sensing and displaying at least one characteristic of a material deposited on a vehicle travel surface, said apparatus comprising:

an electromagnetic radiation transmitter mounted on said vehicle for transmitting a signal toward said material on said vehicle travel surface;

an electromagnetic radiation receiver mounted on said vehicle for receiving a first reflected signal from said vehicle travel surface and a second reflected signal from said deposited material on said vehicle travel surface;

at least one signal processor connected to said receiver for processing said first and second reflected signals and producing a depth output signal corresponding to the thickness of said deposited material.

11. The system according to claim 10 further comprising a second processor connected to said receiver for processing at least one of said reflected signals, comparing the reflected signal to said transmitted signal to determine a characteristic of said deposited material and comparing said characteristic to said information in said database to identify the composition of said deposited material and generate a composition output signal.

12. The system according to claim 11 further comprising a third processor connected to said receiver for comparing said reflected and transmitted signals to determine the density of said deposited material and generating, a density output signal.

13. The system according to claim 12 further comprising a computer connected to said processors wherein said computer receives said density output signal, said composition output signal, and said depth output signal and calculates the amount of a user inputted composition needed to be applied to said vehicle travel surface to produce a desired composition on said surface.

14. The system according to claim 12 further comprising an infrared transceiver mounted on said vehicle connected to a temperature processor for generating an output signal to said computer corresponding to the temperature of said vehicle travel surface.

15. A system carried by a vehicle for remotely sensing and displaying at least one characteristic of a material deposited on a vehicle travel surface, said apparatus comprising:

an electromagnetic radiation transmitter mounted on said vehicle for transmitting a signal toward said material on said vehicle travel surface;

an electromagnetic radiation receiver mounted on said vehicle for receiving a first reflected signal from said vehicle travel surface and a second reflected signal from said deposited material on said vehicle travel surface;

at least one signal processor connected to said receiver for processing at least one of said first and second reflected signals and producing an output signal corresponding to at least one characteristic of said deposited material.

16. The system according to claim 15 further comprising a second processor connected to said receiver for processing at least one of said reflected signals, comparing the reflected signal to said transmitted signal to determine another characteristic of said deposited material and comparing said characteristics to identify the composition of said deposited material and generate a composition output signal.

17. The system according to claim 16 further comprising a third processor connected to said receiver for comparing said reflected and transmitted signals to determine the density of said deposited material and generating a density output signal.

18. The system according to claim 17 further comprising a computer connected to said processors wherein said computer receives said composition output signal and said density output signal and calculates the amount of a user inputted composition needed to be applied to said vehicle travel surface to produce a desired composition on said surface.

19. The system according to claim 15 further comprising a temperature sensor mounted on said vehicle connected to a temperature processor for generating an output signal corresponding to the temperature of said vehicle road surface.

20. The system according to claim 19 further comprising a second processor connected to said receiver for processing at least one of said reflected signals, comparing the reflected signal to said transmitted signal to determine another characteristic of said deposited material and comparing said characteristics to identify the composition of said deposited material and generate a composition output signal.

21. The system according to claim 20 wherein further comprising a computer connected to said temperature processor and composition processor output signals for determining a predicted freeze temperature of said deposited material on said vehicle travel surface.

22. The system according to claim 21 wherein said computer connected to said processors calculates the amount of a user inputted composition needed to be applied to said vehicle travel surface to produce a desired composition on said surface.

23. The system according to claim 22 wherein said computer generates a control output signal for automatic control of chemical addition to said vehicle travel surface.

24. A system carried by a vehicle for remotely sensing and displaying at least one characteristic of a material deposited on a vehicle travel surface, said apparatus comprising:

an electromagnetic radiation transmitter mounted on said vehicle for transmitting a signal toward said material on said vehicle travel surface;

an electromagnetic radiation receiver mounted on said vehicle for receiving a reflected signal from said deposited material on said vehicle travel surface;

at least one signal processor connected to said receiver for processing said reflected signal and producing an output signal corresponding to at least one characteristic of said deposited material;

a database containing information representing various characteristic values for potential deposited materials; and a computer connected to said processor and to said database for comparing said output signal to information in said database and generating a corresponding display signal.

25. The system according to claim 24 further comprising an infrared sensor mounted on said vehicle connected to a temperature processor for generating an output signal to said computer corresponding to the temperature of said vehicle travel surface.

26. The system according to claim 24 further comprising a second signal processor connected to said receiver and to said database and to said computer for processing said reflected signal and comparing the reflected signal to said transmitted signal to determine another characteristic of said deposited material and comparing said characteristic to said information in said database to identify the composition of said deposited material and generate a composition output signal.

27. The system according to claim 26 wherein one of said processors generates an output signal corresponding to the density of said deposited material.

28. The system according to claim 27 wherein said computer receives said density output signal and said composition output signal and calculates the amount of a user inputted composition needed to be applied to said vehicle travel surface to produce a desired composition on said surface.

29. The system according to claim 24 further comprising a second signal processor connected to said receiver for processing said first and second reflected signals and producing a depth output signal corresponding to the thickness of said deposited material.

30. The system according to claim 29 further comprising one of said processors comparing the reflected signal from said deposited material to said transmitted signal to said information in said database to identify the composition of said deposited material and generate a composition output signal.

31. The system according to claim 30 further comprising a third processor connected to said receiver for comparing said reflected and transmitted signals to determine the density of said deposited material and generating a density output signal.

32. The system according to claim 31 wherein said computer receives said density output signal, said composition output signal, and said depth output signal and calculates the amount of a user inputted composition needed to be applied to said vehicle travel surface to produce a desired composition on said surface.

33. The system according to claim 32 wherein said computer generates a control output signal for automatic control of chemical addition to said vehicle travel surface.

34. The system according to claim 31 further comprising an infrared transceiver mounted on said vehicle connected to a temperature processor for generating an output signal to said computer corresponding to the temperature of said vehicle road surface.

* * * * *